United States Patent
Wheeler et al.

(10) Patent No.: US 7,862,780 B2
(45) Date of Patent: Jan. 4, 2011

(54) APPARATUS AND METHOD OF MAKING TRANSFORMED WATER

(76) Inventors: David Wheeler, 8196 SW., Hall Blvd., Suite 108, Beaverton, OR (US) 97008; Nora Kosztolanyi, 8196 SW., Hall Blvd., Suite 108, Beaverton, OR (US) 97008

(*) Notice: Subject to any disclaimer, the term of this patent is extended or adjusted under 35 U.S.C. 154(b) by 473 days.

(21) Appl. No.: 11/993,872

(22) PCT Filed: Jun. 13, 2006

(86) PCT No.: PCT/US2006/023028
§ 371 (c)(1), (2), (4) Date: Dec. 24, 2007

(87) PCT Pub. No.: WO2007/008328
PCT Pub. Date: Jan. 18, 2007

(65) Prior Publication Data
US 2010/0086475 A1    Apr. 8, 2010

Related U.S. Application Data

(60) Provisional application No. 60/595,475, filed on Jul. 8, 2005.

(51) Int. Cl.
*B01J 19/00* (2006.01)
*C02F 1/48* (2006.01)
*C01B 5/00* (2006.01)

(52) U.S. Cl. .......... 422/129; 210/222; 210/223; 210/695; 423/580.1

(58) Field of Classification Search ............. 422/129; 423/580.1; 210/222, 223, 232, 322, 695
See application file for complete search history.

(56) References Cited

U.S. PATENT DOCUMENTS 5,711,950 A    1/1998    Lorenzen (Continued)

OTHER PUBLICATIONS

I. Jerman, Information processing in water and fields, in Proceedings of the 6th International Multi-Conference Information Society—Cognitive Sciences, Ljubljana, Slovenia, 2003.

(Continued)

*Primary Examiner*—Walter D Griffin
*Assistant Examiner*—Natasha Young
(74) *Attorney, Agent, or Firm*—Bert P. Krages, II

(57) ABSTRACT

The present invention provides an apparatus and method of producing transformed water without contact between the original transformed water and the water to be transformed. This is accomplished by organizing the original transformed water into a geometric contained arrangement such that a central cavity is created that substantially surrounds the water that is to be transformed. The water to be transformed is placed into a confined vessel such as a cylindrical container or a pipe inside the central cavity for about sixty seconds. This water then becomes transformed in the same likeness of the molecular clustering of the original transformed water.

20 Claims, 5 Drawing Sheets

U.S. PATENT DOCUMENTS

| | | | |
|---|---|---|---|
| 5,800,576 A * | 9/1998 | Johnson et al. | 44/301 |
| 5,800,779 A | 9/1998 | Johnson | |
| 5,846,397 A | 12/1998 | Manzatu | |
| 5,997,590 A * | 12/1999 | Johnson et al. | 44/301 |
| 6,033,678 A * | 3/2000 | Lorenzen | 424/401 |
| 6,103,218 A | 8/2000 | Brucker | |
| 6,139,855 A | 10/2000 | Cioca | |
| 6,165,339 A * | 12/2000 | Ibbott | 204/554 |
| 6,451,328 B1 | 9/2002 | Ionita-Manzatu | |
| 6,521,248 B1 | 2/2003 | Holloway | |
| 2002/0179536 A1 | 12/2002 | Lee | |
| 2003/0028070 A1 | 2/2003 | Jacobson | |
| 2004/0126468 A1 | 7/2004 | Holloway | |
| 2004/0234618 A1 | 11/2004 | Saito | |
| 2004/0251211 A1 | 12/2004 | Suddath | |

OTHER PUBLICATIONS

L. Rey, Thermoluminescence of ultra-high dilutions of lithium chloride and sodium chloride, Physica A 323 (2003) 67-74, Elsevier Inc., New York, New York.

J. Benveniste, et. al., The Molecular Signal Is Not Functional in the Absence of "Informed" Water, FASEB Journal, 1999, vol. 13, p. A163), Federation of American Societies for Experimental Biology, Bethesda, MD.

J. Benveniste, et. al., A simple and fast method for in vivo demonstration of electromagnetic molecular signaling (EMS) via high dilution or computer recording, FASEB Journal 1999, vol. 13, p. A163, Federation of American Societies for Experimental Biology, Bethesda, MD.

* cited by examiner

APPARATUS AND METHOD OF MAKING TRANSFORMED WATER

CROSS REFERENCE TO RELATED APPLICATIONS

This application claims the benefit to the prior provisional patent application 60/595,475 filed Jul. 8, 2005, the filing date of which is hereby claimed and which application is hereby adopted by reference as part of the present disclosure.

FIELD OF THE INVENTION

The invention relates generally to a method for the synthesis of transformed water to produce water that is useful in applications such as increasing cellular hydration in living organisms.

BACKGROUND OF THE INVENTION

Water is composed of molecules consisting of two hydrogen atoms that are covalently attached to an oxygen atom in the form of a polar bond. The polar bonds are characterized by a small localized negative charge around the oxygen atom and a small localized positive charge around the hydrogen atoms. These partial charges enable water molecules to bind up with other water molecules in ways that can result in various lattice arrangements. Once a form of hydrogen bonding has occurred, the redistribution of electrons alters the ability for further hydrogen bonding. Under proper conditions, the water molecules will associate themselves into small clusters that behave differently in many ways from molecules in the bulk water form (such as commonly exists in tap water).

There are various means of inducing water molecules to arrange themselves into small clusters that possess particular properties such as frequency and electromagnetic resonance. Such means include the application of concussive forces that may include vortex motion, the addition of minerals and solids, the addition of gases, ionization, contact with electricity, and the application of strong or weak magnetic forces. Properly done, such means can produce water clusters that have specific frequencies and stabilities. The form of water thus produced is called transformed water.

One form of such clusters has a closed symmetry formed by twenty hydrogen-bonded water molecules, also known as a dodecahedral water cluster. However, there are other forms of clustered water in which the clusters may be smaller or larger. Such clusters can be made to possess a stable structure with a water transfer memory property that can cause other molecules to respectively align themselves in specific ways.

Water memory transfer is defined as the capacity of water molecules to memorize the specific structure and frequency of other water molecules. One means of transferring water memory to untransformed water is to add a solute to a batch of transformed water and dilute it with untransformed water. This will result in the untransformed diluent water taking on the character of the transformed water. Water memory can also be transferred by electromagnetic molecular signaling to likewise convert untransformed water into a transformed water with specific molecular cluster properties. J. Benveniste, J. Aïssa and D. Guillonnet, A Simple and Fast Method for in Vivo Demonstration of Electromagnetic Molecular Signaling (EMS) via High Dilution or Computer Recording, *FASEB Journal*, 1999, vol. 13, p. A 163.

SUMMARY OF THE INVENTION

The present invention provides an apparatus and method of producing transformed water without contact between original transformed water and the water to be transformed. This is accomplished by organizing an amount of original transformed water with a very high level of stored energy into a geometric arrangement that substantially surrounds the water that is to be transformed. The water to be transformed is placed into a confined vessel such as a cylindrical container or a pipe inside the central cavity for about sixty seconds. This water then becomes transformed in the same likeness of the molecular clustering of the original transformed water but at a lower level of stored energy.

The invention can be operated in static and continuous flow versions. In a static version, the original transformed water is placed within a container which is inserted into the central cavity for the requisite time. This manner of operation allows for the making of transformed water on a batch basis and is particular useful for making transformed water from untransformed water that has already been containerized such as commercially available bottled water. In a continuous-flow version, a pipe is installed within the central cavity such that it has substantially the same dimensional relationship as found in a static version. Untransformed water is conveyed through the pipe from a proximal end of the central cavity to the distal end, at a flow rate that ensures that the residence time of the water within the space defined by the central cavity is about sixty seconds. The water is transformed during its passage through the section of pipe encompassed by the central cavity and thus converted into a transformed state by the time it exits the pipe at the distal end of the central cavity.

DESCRIPTION OF THE PREFERRED EMBODIMENT

Figure 1:
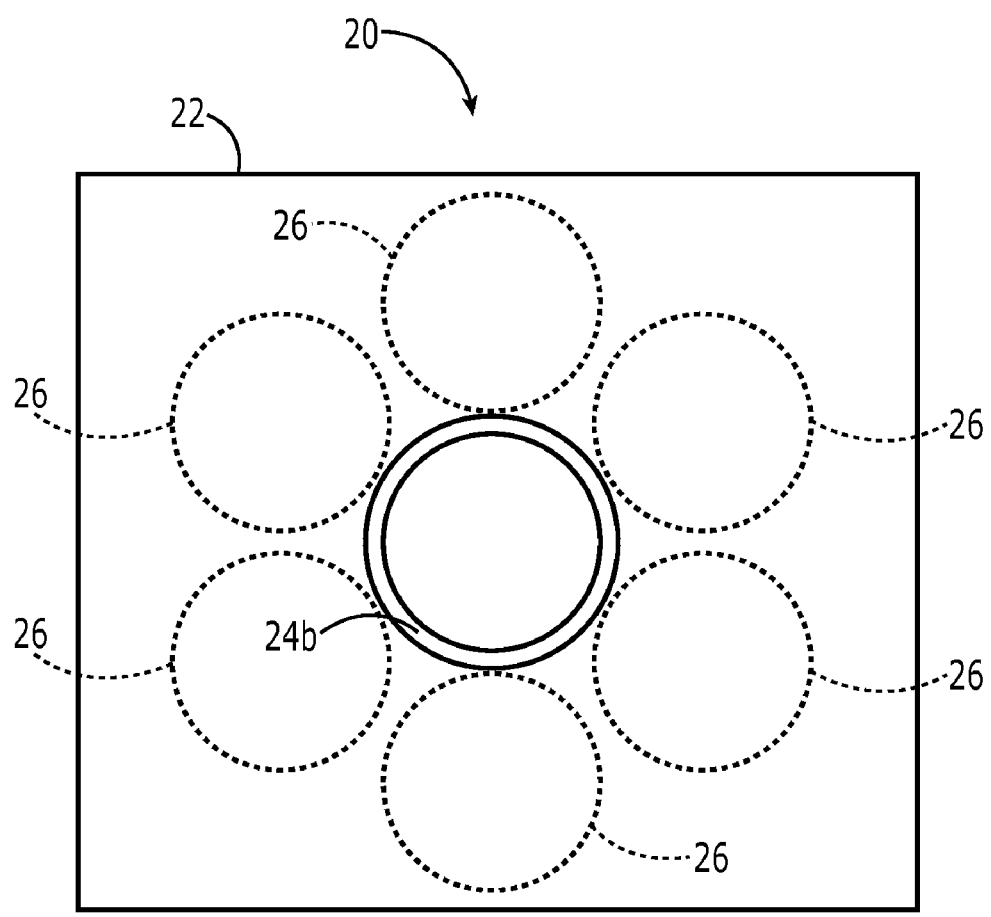
FIG. 1 is a top view of the invention in a static version.
Figure 2:
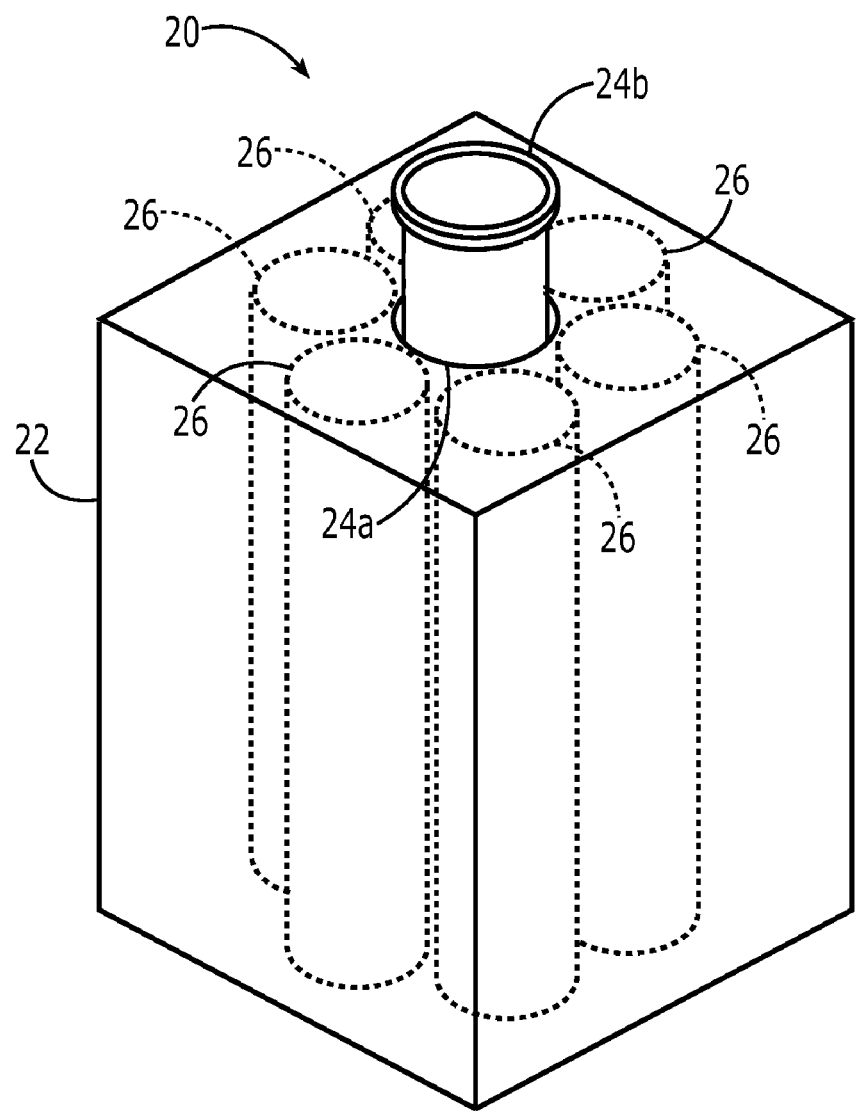
FIG. 2 is a perspective view of the invention in a static version.

FIG. 1 and FIG. 2 show the overall invention 20 in an embodiment that allows for the manufacture of transformed water in batches. The invention is housed in a structure 22 that in the preferred embodiment comprises six substantially cylindrical containers 26 that are filled with transformed water. The containers are disposed radially around a substantially cylindrical central cavity 24a in an evenly spaced manner as close as possible to each other so that a substantially cylindrical space is defined within the inner boundaries of the containers 26. A vessel 24b may be filled with water to be transformed and inserted inside the central cavity 24a. Said vessel can constitute any configuration capable of holding water although in the preferred embodiment the vessel will have a substantially cylindrical shape that is slightly smaller in diameter than the central cavity 24a. It should be noted that any number of containers 26 may be used provided that they can be evenly disposed around the central cavity 24a. For example, a single container could comprise inner and outer walls consisting of concentric cylinders with a solid bottom end so that the space between said inner and outer walls will hold transformed water and the space inside said inner wall will constitute the central cavity 24a. If a plurality of containers is used to hold the transformed water, they should be smaller in diameter than the central cavity 24a when three to five containers are used, about the same diameter as the central cavity 24a when six containers are used, and smaller in diameter than the central cavity 24a when seven or more containers are used.

To transform the water in vessel 24b, said vessel is placed within the central cavity 24a where it is thus surrounded by containers 26 filled with transformed water. The vessel containing the water to be transformed should be left inside the central cavity 24a for at least sixty seconds, at which time it will have become transformed to the same likeness as the clusters of the transformed water in the containers 26 albeit at a lower level of stored energy.

Figure 3:
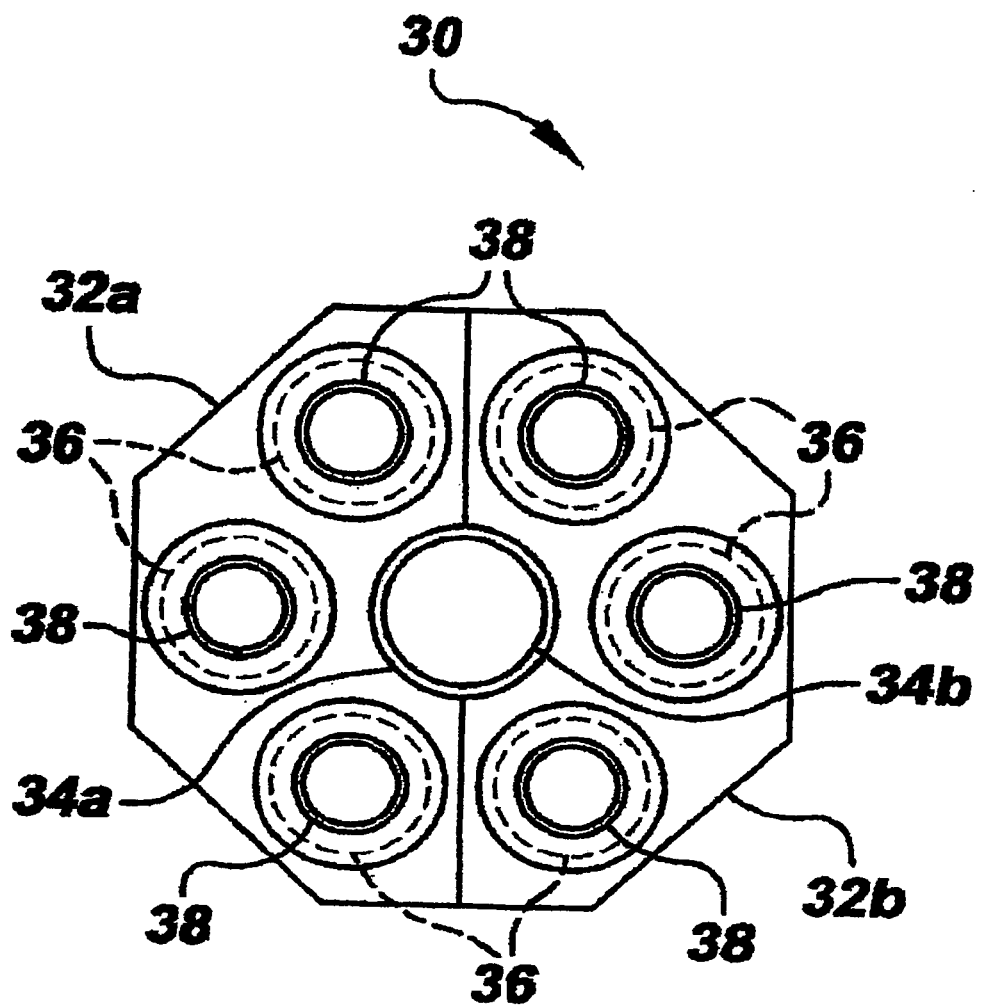
FIG. 3 is a top view of the invention in a continuous flow version.
Figure 4:
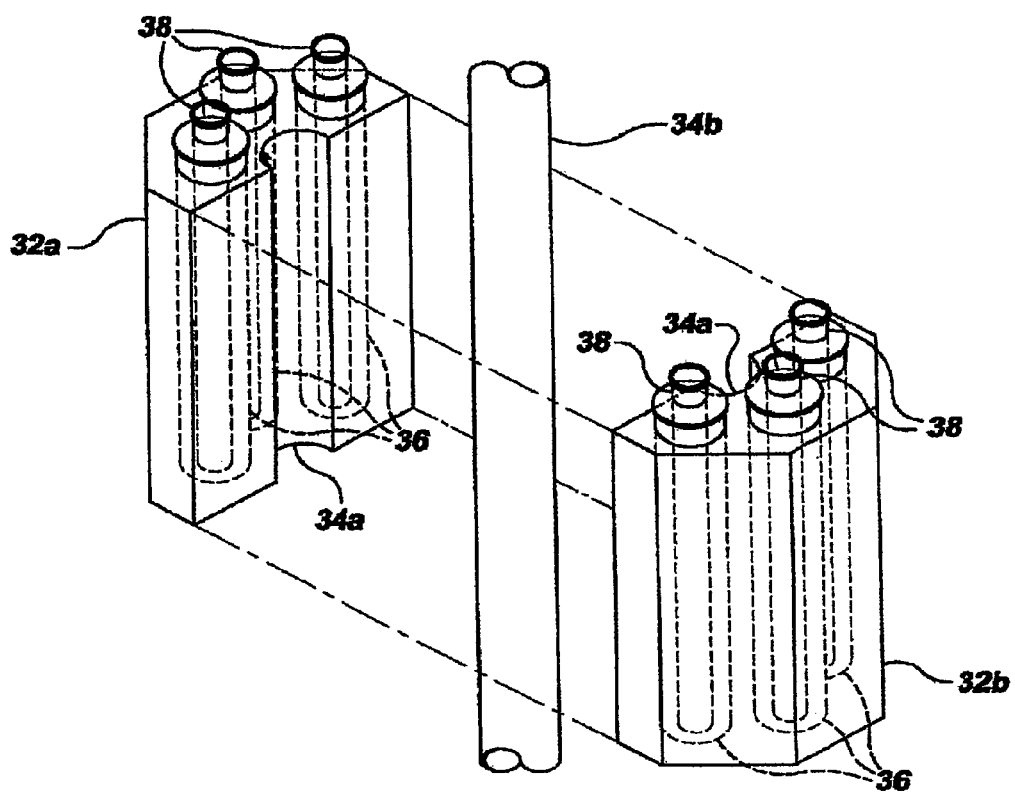
FIG. 4 is an exploded perspective view of the invention in a continuous flow version.
Figure 5:
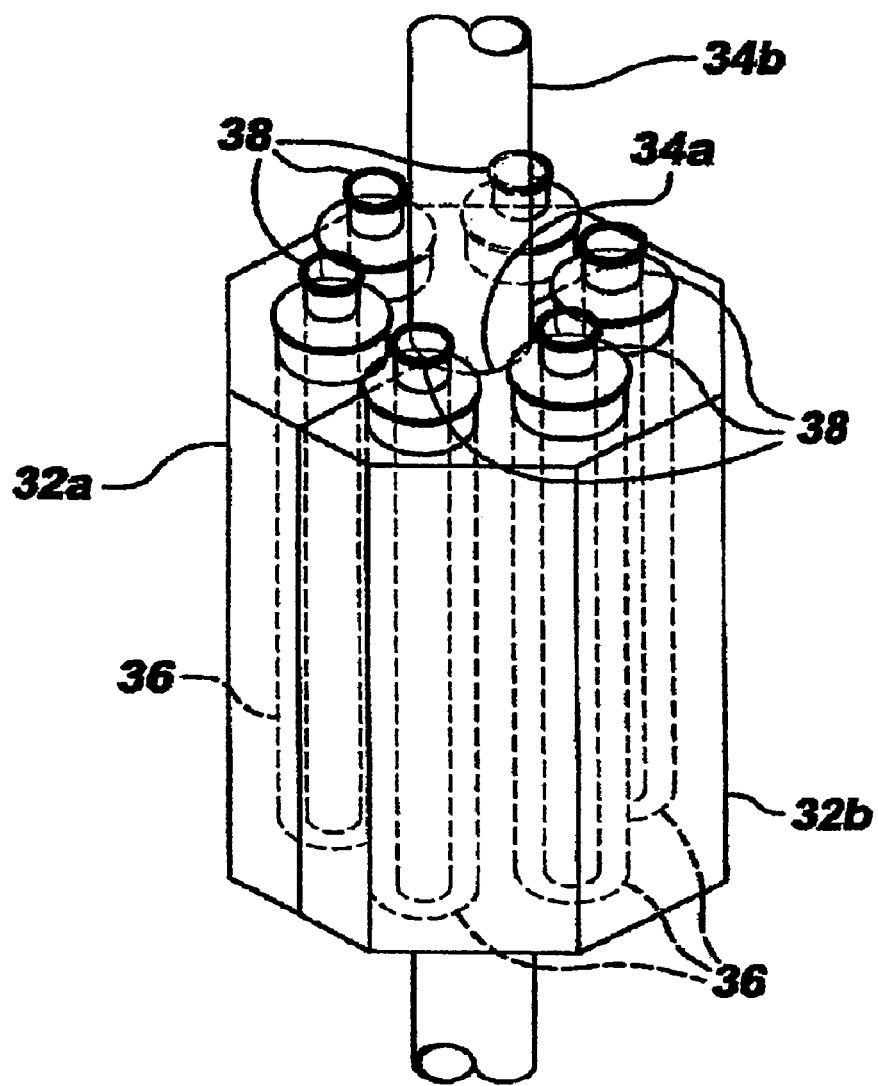
FIG. 5 is an assembled perspective view of the invention in a continuous flow version.

FIG. 3, FIG. 4, and FIG. 5 show the overall invention 30 in an another embodiment that allows for water to be transformed in a continuous-flow mode. In the preferred embodiment of the continuous-flow mode, three substantially-cylindrical containers 36 are disposed in one half of a hexagonal shell 32a such that they substantially form a semicircle. Three other substantially-cylindrical containers are further disposed in an opposing half of a hexagonal shell 32b such that they substantially form a semicircle oriented in the opposite direction of the semicircular shape associated with shell 32a. A central cavity 34a is formed when the shells 32a and 32b are brought together as shown in FIG. 3 and FIG. 5. When the shells 32a and 32b are brought together and secured over a pipe 34b, the central cavity 34a will encompass said pipe and situate it in close proximity to the containers 36.

To transform the water in pipe 34b, the first step in the preferred embodiment of the Continuous-flow mode is to bring the shells 32a and 32b together to encompass the pipe 34b inside the central cavity 34a. Transformed water is then poured into the cylindrical containers 36 through open orifices 38 located at the topside ends of said containers. Untransformed water is then brought to flow through the pipe 34b at a flow rate sufficient to ensure that residence time of the water within the section of pipe 34b encompassed by the central cavity 34a is at least sixty seconds. The water will be transformed during the time it resides within the section of pipe 34b encompassed by the central cavity 32a, and be completely transformed upon exiting such section of pipe. Means of inducing and controlling flow within pipe 34b are well known in the art and include pumps, gravity, valves, and petcocks. It should also be noted that alternative embodiments could use containers 36 in various arrangements comprising one or more containers such as those described above for the static mode embodiment. Those of ordinary skill in the art will recognize that the foregoing descriptions cover certain preferred embodiments of the invention. Various modifications can be made to the particular embodiments described without departing from the spirit and scope of the invention. All such changes and modifications are incorporated within the scope of the following claims.

We claim:

1. An apparatus for manufacturing transformed water comprising a vessel containing water to be transformed that is disposed within a central cavity surrounded by transformed water.

2. The apparatus of claim 1 wherein said central cavity is disposed with the space defined by the inside surface of a cylindrical inner wall and said transformed water is contained in a single container that comprises said cylindrical inner wall and an outer wall.

3. The apparatus of claim 1 wherein said transformed water is contained in two or more containers disposed radially around said central cavity.

4. The apparatus of claim 1 wherein said vessel constitutes a pipe.

5. An apparatus for manufacturing transformed water comprising a vessel containing water to be transformed that is disposed within a central cavity surrounded by transformed water having at least partial dodecahedral symmetry.

6. The apparatus of claim 5 wherein said central cavity is disposed with the space defined by the inside surface of a cylindrical inner wall and said transformed water is contained in a single container that comprises said cylindrical inner wall and an outer wall.

7. The apparatus of claim 5 wherein said transformed water is contained in two or more containers disposed radially around said central cavity.

8. The apparatus of claim 5 wherein said vessel constitutes a pipe.

9. A method of manufacturing transformed water in which a vessel containing the water to be transformed is placed within a central cavity surrounded by transformed water and retained in said central cavity for an effective amount of time.

10. The method of claim 9 in which said effective amount of time is at least 60 seconds.

11. The method of claim 9 in which said vessel is a pipe.

12. The method of claim 9 wherein said central cavity is disposed with the space defined by the inside surface of a cylindrical inner wall and said transformed water is contained in a single container that comprises said cylindrical inner wall and an outer wall.

13. The method of claim 9 wherein said central cavity is disposed with the space defined by the inside surface of a cylindrical inner wall, said transformed water is contained in a single container that comprises said cylindrical inner wall and an outer wall, and said effective amount of time is at least 60 seconds.

14. The method of claim 9 wherein said central cavity is disposed with the space defined by the inside surface of a cylindrical inner wall, said transformed water is contained in a single container that comprises said cylindrical inner wall and an outer wall, said vessel constitutes a pipe, and said water to be transformed is retained in the section of said pipe encompassed by said central cavity for said effective amount of time.

15. The method of claim 9 wherein said central cavity is disposed with the space defined by the inside surface of a cylindrical inner wall, said transformed water is contained in a single container that comprises said cylindrical inner wall and an outer wall, said vessel constitutes a pipe, and said water to be transformed is retained in the section of said pipe encompassed by said central cavity for said effective amount of time which is at least 60 seconds.

16. The method of claim 9 wherein said transformed water is contained in two or more containers disposed radially around said central cavity.

17. The method of claim 9 wherein said transformed water is contained in two or more containers disposed radially around said central cavity and said effective time is at least 60 seconds.

18. The method of claim 9 wherein said transformed water is contained in two or more containers disposed radially around said central cavity, said vessel constitutes a pipe, and said water to be transformed is retained in the section of said pipe encompassed by said central cavity for said effective amount of time.

19. The method of claim 9 wherein said transformed water is contained in two or more containers disposed radially around said central cavity, said vessel constitutes a pipe, and said water to be transformed is retained in the section of said pipe encompassed by said central cavity and said effective amount of time is at least 60 seconds.

20. The method of claim 9 wherein said transformed water is contained in three or more containers disposed radially around said central cavity, said effective time is at least-60 seconds, and said transformed water has at least partial dodecahedral symmetry.

* * * * *